US00PP25274P3

(12) United States Plant Patent
Egger

(10) Patent No.: US PP25,274 P3
(45) Date of Patent: Jan. 27, 2015

(54) ***AGASTACHE* PLANT NAMED 'VIOLET VISION'**

(50) Latin Name: ***Agastache* hybrid**
Varietal Denomination: Violet Vision

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 47 days.

(21) Appl. No.: 13/986,386

(22) Filed: Apr. 26, 2013

(65) Prior Publication Data

US 2014/0325722 P1 Oct. 30, 2014

(51) Int. Cl.
*A01H 5/00* (2006.01)

(52) U.S. Cl.
USPC ..... Plt./399

(58) Field of Classification Search
CPC ..... A01H 5/00; A01H 5/02
USPC ..... Plt./399
See application file for complete search history.

(56) References Cited

PUBLICATIONS

Terra Nova website 2014.*
Garden Center Magazine 2012.*
UPOV Record Detail 2014.*

* cited by examiner

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Agastache* plant characterized by violet blue flowers in large inflorescences, a long bloom time, a short, compact habit, good winter hardiness, and excellent vigor.

1 Drawing Sheet

Botanical denomination: *Agastache* hybrid.
Variety designation: 'Violet Vision'.

BACKGROUND

The present invention relates to a new and distinct cultivar of *Agastache,* given the name, 'Violet Vision'. *Agastache* is in the family Lamiaceae. This new variety is one of several selections of new *Agastache* using *Agastache cusickii* and *A. rugosa* in the breeding lines to provide hardiness and compactness. The new cultivar is a selection from the cross between the proprietary seedlings 09-02T, as the seed parent, and (08-2T×08-1T)#8, as the pollen parent. The new cultivar was selected for its compact habit, hardiness, and violet blue flowers.

Compared to the seed parent, *Agastache* 09-02T (unpatented) the new cultivar is shorter and has violet blue rather than purple blue flowers.

Compared to the pollen parent, *Agastache* (08-2T×08-1T) #8 (unpatented), the new cultivar has violet blue rather than white flowers and is taller and upright rather than prostrate.

Compared to *Agastache* 'Blue Boa', U.S. Plant Pat. No. 24,050, the new cultivar has lighter colored flowers and is much shorter.

This plant exhibits the following characteristics that make it unique:

1. violet blue flowers in large inflorescences,
2. a long bloom time,
3. a short, compact habit,
4. good winter hardiness,
5. and excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the new cultivar growing in a one gallon container outside in full sun in Canby, Oreg.

FIG. 2 shows a bed of nine-month-old *Agastache* 'Violet Vision' growing in the field in mid summer in Canby, Oreg.

DETAILED PLANT DESCRIPTION

The following is a detailed description of the new *Agastache* cultivar based on observations of 10-month-old specimens in October growing outside in full sun in a one gallon container in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Upright.

*Type.*—Herbaceous perennial.

*Cold hardiness.*—USDA Zone 6-10.

*Size.*—Grows to 25 cm wide and 58 cm tall to the top of the flowers.

*Vigor.*—Excellent, fast growth rate.

*Branching.*—About 10 main stems from the base, these branch at every node.

*Stem.*—Square in cross section, grows to 15 mm wide at the base and 18 cm tall to the first flower, pubescent, internodes range from 3 to 10 cm long, Yellow Green 146B.

*Roots.*—White NN155B, fibrous, plants root easily from stem tip cuttings.

Leaf:

*Type.*—Simple.

*Arrangement.*—Opposite.

*Shape.*—Ovate.

*Venation.*—Pinnate.

*Margins.*—Coarsely serrate.

*Apex.*—Acute.

*Base.*—Cuneate and auriculate; with the base cuneate for about 3 mm then auriculate.

*Blade size.*—Grows to 43 mm long and 40 mm wide.

*Surface texture.*—Pubescent on both sides.

*Petiole description.*—16 mm long and 1.5 mm wide, pubescent, Yellow Green 147B.

*Leaf color.*—Top side Green N137A with vein Green 137C, bottom side closest to Yellow Green 147B with vein 147C.

*Fragrance.*—Aromatic.

Inflorescence:

*Type.*—Terminal spike with up to 12 whorls.

*Number of flowers.*—Up to 600 per spike.

*Size of inflorescence.*—Grows to 19 cm tall and 5 cm wide.

*Peduncle.*—Grows to 20 cm tall and 3 mm wide, pubescent, Yellow Green 146A.

*Pedicel.*—Grows to 2 mm long, pubescent, Grey Brown 199C.

*Bloom period.*—June through frost in Canby, Oreg.

Flower bud:

*Size.*—16 mm long and 3 mm wide at the widest point prior to opening.

*Description.*—Tubular.

*Surface texture.*—Pubescent.

*Color.*—Purple N79B.

Flower:

*Type.*—Zygomorphic.

*Shape.*—Bilabiate, tubular.

*Size.*—24 mm long and 7 mm wide.

*Corolla description.*—23 mm long and spreads to 7 mm wide; color both sides Violet 83C; pubescent inside and outside, tube 12 mm long and 1 mm to 4 mm wide; 2 upper lobes joined, each 3 mm long and 3 mm wide, each ovate, tips obtuse, margin entire; three lower lobes, two spreading sideways and curve out slightly, each 1.5 mm long and 2.5 mm wide, tip obtuse, margin entire; bottom lobe, reflexed, broadly obovate, notched at the tip, margin undulate, 5 mm wide and 2.7 mm deep.

*Calyx description.*—Campanulate, 9 mm long and 3.5 mm wide, pubescent outside and glabrous inside, 5 lobed, lobes triangular, 2.7 mm long, entire, acuminate, color closest to Purple N79A.

*Pistil description.*—27 mm long, exerted, ovary 1.5 mm long, Yellow Green 145D, style 25 mm long, Violet 85D at bottom blending to Violet 83A at top, stigma two-parted, 0.5 mm deep, Violet 83A.

*Stamen description.*—4 in number, paired and exerted, top two 9 mm long and bottom two 6 mm long, filaments Violet N82A, anthers 0.3 mm long, Violet Blue 86A, pollen White N155A.

*Fragrance.*—Aromatic.

*Lastingness.*—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

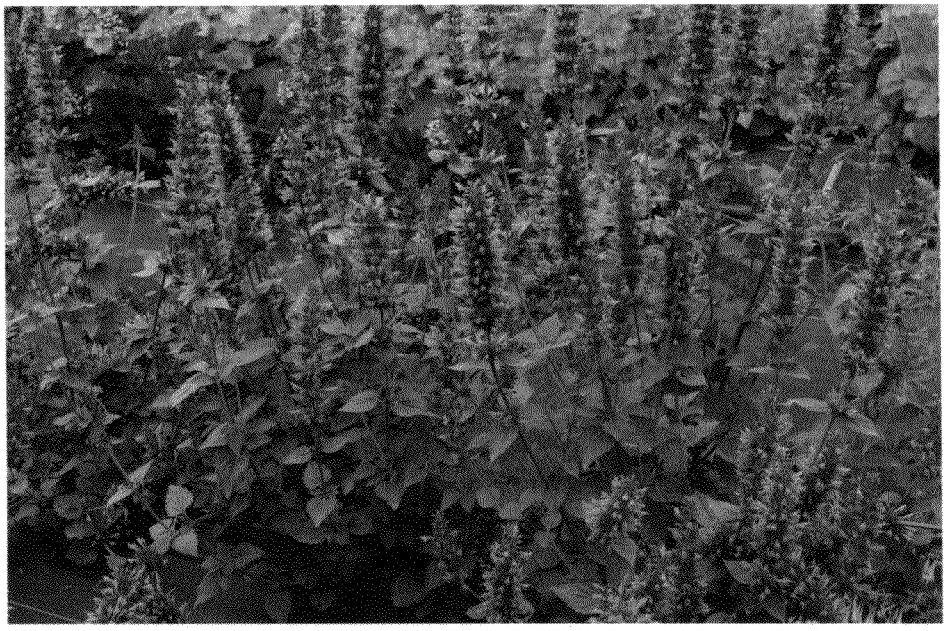

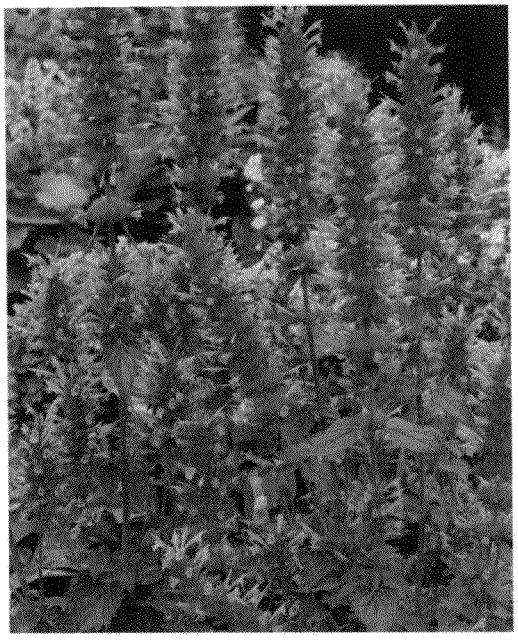
FIG. 1 on left
FIG. 2 below